(12) United States Patent
Halderman et al.

(10) Patent No.: US 7,770,467 B1
(45) Date of Patent: Aug. 10, 2010

(54) FIXTURE FOR MECHANICAL ANALYSIS OF A HOLLOW TUBE

(75) Inventors: Jonathan Halderman, Santa Clara, CA (US); James Oberhauser, Saratoga, CA (US); Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 30 days.

(21) Appl. No.: 12/245,588

(22) Filed: Oct. 3, 2008

Related U.S. Application Data

(60) Provisional application No. 61/086,100, filed on Aug. 4, 2008.

(51) Int. Cl.
*G01N 3/02* (2006.01)
(52) U.S. Cl. .......................................... 73/856; 73/849
(58) Field of Classification Search .................... 73/856, 73/849
See application file for complete search history.

(56) References Cited

U.S. PATENT DOCUMENTS

| | | | | |
|---|---|---|---|---|
| 5,710,426 A * | 1/1998 | Reed et al. | ............... | 250/237 G |
| 7,363,821 B2 * | 4/2008 | Black et al. | .................... | 73/810 |
| 7,472,604 B2 * | 1/2009 | Moore et al. | .................. | 73/849 |
| 7,552,650 B2 * | 6/2009 | Phelan et al. | ................. | 73/856 |
| 2004/0219659 A1 * | 11/2004 | Altman et al. | ........... | 435/284.1 |
| 2006/0020330 A1 | 1/2006 | Huang et al. | | |
| 2007/0068274 A1 * | 3/2007 | Olson et al. | .................... | 73/788 |
| 2009/0012598 A1 | 1/2009 | Abbate et al. | | |
| 2010/0000329 A1 * | 1/2010 | Lorenz et al. | ................. | 73/856 |

* cited by examiner

*Primary Examiner*—Lisa M Caputo
*Assistant Examiner*—Freddie Kirkland, III
(74) *Attorney, Agent, or Firm*—Squire, Sanders & Dempsey L.L.P.

(57) ABSTRACT

A test fixture for use with a Dynamic Mechanical Analyzer (DMA) restrains a hollow cylindrical tube for purposes of performing either a tensile or transverse/bending load test. The fixture includes a clamp that is configured to restrain the tube without imparting a preload or changing a mechanical property of the tube.

15 Claims, 13 Drawing Sheets

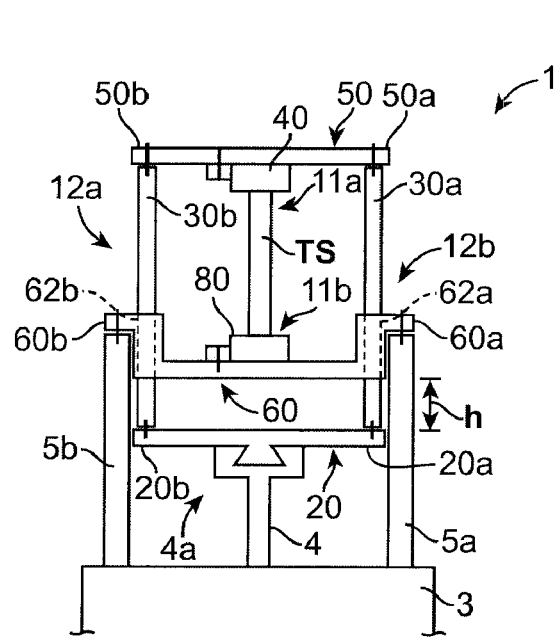
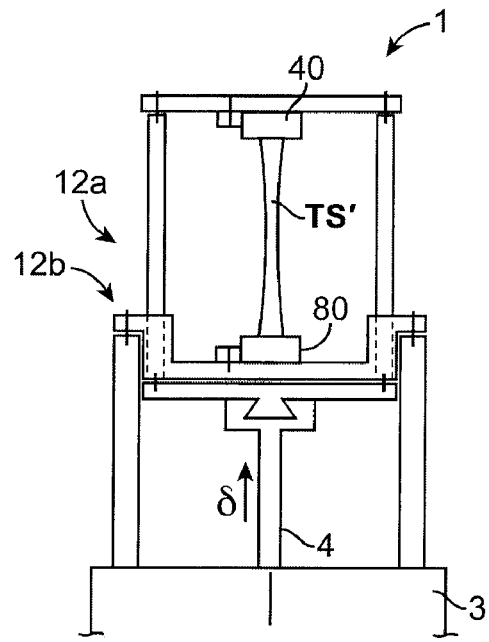
FIG. 1A    FIG. 1B
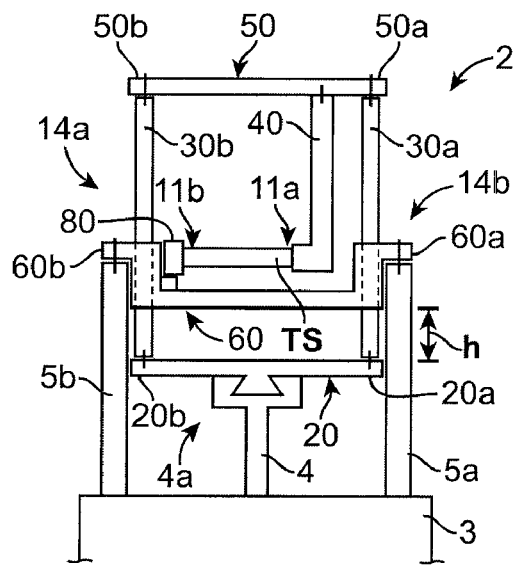
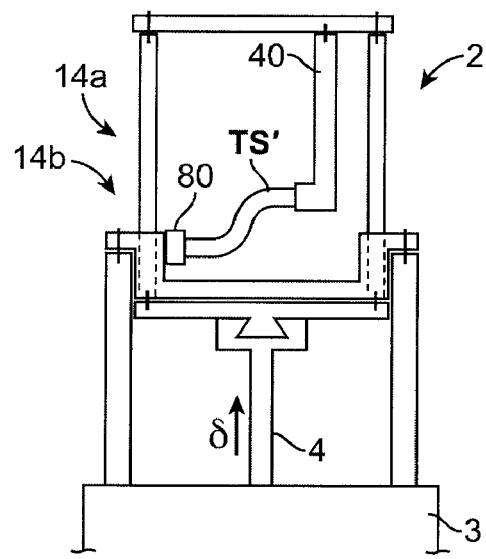
FIG. 2A    FIG. 2B ured to be determined in the body is raised. The stiffness and damping can be controlled by varying the mode of the sample, which is a function of the temperature.

FIXTURE FOR MECHANICAL ANALYSIS OF A HOLLOW TUBE

This application claims the benefit of U.S. Provisional Application Ser. No. 61/086,100, filed Aug. 4, 2008, the contents of which are incorporated by reference in its entirety.

BACKGROUND OF THE INVENTION

1. Field of the Invention

The present invention relates to mechanical analysis of a material used to make a medical device or portions thereof intended for implantation within a body; more particularly, this invention relates to mechanical analysis of a polymeric material represented by a hollow tube having dimensions approximating the dimensions of a medical device, such as a stent.

2. Background of the Invention

A Dynamic Mechanical Analyzer (DMA) is a precision instrument designed to measure the viscoelastic properties of a material, such as a polymer material in a dry or wet stage. A DMA may be used to measure changes in a sample material resulting in changes in temperature and/or external forces. Applied external forces may be represented by enforced displacements on the sample, in which case material properties are determined from a measured reaction force. The external forces may be time-varying, e.g., sinusoidal. Prior to testing, a sample of the material is mounted in a clamp, one part of which is stationary and the other part is moving and connected to a motor drive.

The sample can be in a bulk solid, film, fiber, gel or viscous form depending on the fixture used. The motor drives the sample to a selected strain or amplitude. As the sample undergoes deformation, a linear variable differential transformer mounted on a driving arm or rod measures such quantities as a static or time-varying strain amplitude as feedback control to the motor. Interchangeable fixtures are used to measures quantities such as an elastic modulus, toughness, damping, stress relaxation, creep, and softening points. See e.g., *Introduction to Dynamic Mechanical Analysis (DMA)—A beginner's Guide*, PerkinElmer® Inc.

One quantity of importance in analyzing material used to make implantable medical devices is the glass transition temperature, $T_g$. The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

The sample and the fixture restraining the sample is enclosed within a thermal isolation chamber which can heat the sample and the fixtures to temperatures above normal ambient temperatures or cool the sample and the fixtures to temperatures below normal ambient temperatures. The temperature is generally varied dynamically, e.g., at a constant heating or cooling rate. The stiffness and damping of a sample may be calculated as a function of temperature from force, displacement and phase data, using well-known mathematical relationships which separate the applied load into the components due to movement of the mechanical system and the components due to deformation of the sample. The phase relationship between the force applied to the sample and the resultant displacement allows the sample deformation force component to be further divided into an elastic component and a viscous component. The elastic and viscous components are used to determine the elastic modulus and damping through the use of model equations for the particular sample geometry and deformation mode. These equations are well-known in the field, e.g., Theory of Elasticity, S. P. Timoshenko and J. N. Goodier, McGraw-Hill (3rd ed. 1970). Currently, there are two classes of fixtures for DMA—tensioning and non-tensioning. Tensioning fixtures include the 3-point bend, tension/film, tension/fiber, compression, compression and penetration fixtures, while non-tension fixtures include single/dual cantilever and shear sandwich fixtures.

As mentioned above, existing fixtures for restraining movement of a sample in a DMA are intended for analysis of material in bulk solid, film, fiber, gel or viscous form. Unfortunately, there exists no ability to test a hollow cylindrical tube, in particular, a thin walled tube having dimensions corresponding to a tube that is formed into a stent. A fixture suited for a film or fiber, for example, cannot restrain a hollow tube in a wet or dry environment, as needed, because either the sample cannot be adequately held by a clamp, the clamp induces unwanted preloads into the sample, such as torsion, or collapses the tube walls when the clamp is tightened down on the ends of the tube in order to hold it in place. Other problems with existing fixtures are they are difficult to assemble or modify to accommodate the special needs of a hollow tube.

SUMMARY OF THE INVENTION

According to the invention, a fixture for a DMA is capable of adequately restraining a hollow cylindrical tube made from a polymer and having dimensions of an implantable medical device, such as a stent. When installed in the fixture, the hollow tube is not pre-stressed as a result of bending, tensile loading or torque applied to the tube by the fixture which effects the ability to accurately measure mechanical properties of the extruded material. The tube is supported at its ends to prevent collapse of the relatively thin walls of the tubing.

According to one aspect of invention, a fixture adapted for performing a tensile or bending load test on a hollow cylindrical tube is provided. In some embodiments, the testing of the hollow tube includes a measurement of the glass transition temperature for a polymer hollow cylindrical tube have approximately the dimensions of a stent, examples of which are discussed in U.S. Pub. No. 20080147165.

According to another aspect of the invention, a clamp portion of the fixture is configured so that no torque preload is applied to the tube when the tube is secured in the clamp. The clamp may be custom made to hold a tube having a prescribed outer diameter.

According to another aspect of the invention, an improved assembly procedure for placing a hollow tube in a fixture is disclosed. The assembly procedure can be applied to either a dry or wet test setup procedure and can be rapidly reproduced for different size tubes.

According to another aspect of the invention, there is a method for assembly, method of testing and/or apparatus for performing dynamic mechanical analysis on a material using DMA, the material taking the form of tubular body that has the dimensions of an extruded polymer tube that will be formed into a stent. In some embodiments, the tube has cylindrical walls. In other embodiments, the tube walls has a stent pattern characteristic of a balloon expandable stent.

According to one embodiment of the invention, a fixture for tensile or bending load testing using a DMA is capable of restraining a hollow cylindrical tube without causing collapse of tube walls or inducing a preload in torsion for a tube having an outer diameter in the range of about 0.4-0.2 inches, and an inner diameter in the range of about 0.01-0.18 inches.

According to another aspect of the invention, an apparatus for determining the mechanical properties of a material includes a base platform including a programmable drive configured to move relative to a stationary post, a test specimen including a hollow cylindrical tube substantially formed from the material and having a first end and a second end, and a test fixture, including: a first mount coupled to the drive and extending upwards therefrom, the first mount including at an upper end thereof a first member adapted for applying pressure about the circumference of the hollow tube first end, and a second mount coupled to the post and disposed over the drive, the first mount including at an upper end thereof a second member adapted for applying pressure about the circumference of the hollow tube second end.

According to another aspect of the invention, a method for predicting a physical property of a material using a mechanical analyzer having a drive and a stationary post includes the steps of coupling one end of a hollow cylindrical tube to a first clamp, the hollow cylindrical tube being substantially formed from the material, coupling the first clamp to the post, coupling a second clamp to the drive, coupling the other end of the hollow cylindrical tube to the second clamp, applying a known load or deflection to the hollow cylindrical tube through the drive, and then measuring the force or displacement of the one end of the hollow cylindrical tube relative to the other end in response to the applied load.

According to another aspect of the invention, an apparatus includes a clamp capable of restraining a polymer hollow cylindrical tube under an idealized boundary condition, e.g., no net torque, during a mechanical analysis, the clamp including a flexible coupling that couples a plurality of fingers to a pair of arms. The plurality of fingers form an approximately circular bearing surface when the arms are brought adjacent to each other, and the flexible coupling is arranged to produce the desired load distribution about the circumference of the tube. The clamp may be a unitary clamp. The flexible coupling may be a ring.

According to another aspect of the invention, an apparatus for determining the mechanical properties of a material includes a testing platform including a drive configured to move relative to a post, a hollow cylindrical tube substantially formed from the material and having a first end and a second end, and a test fixture including means for coupling the hollow tube to the drive and the post without preloading the tube in torsion. The means may include a ring surrounding a plurality of fingers having a bearing surface. The bearing surface is brought into contact with the outer surface of the hollow tube when the tube is secured in the clamp. The ring may have a non-constant thickness, or different thickness, among the fingers for modifying the load distribution from the tube surface to the ring given the applied loading external loading. In this case, the stiffness characteristics of the ring are such that when the fixture is subjected to a predetermined applied load, there can be a uniform loading of the tube surface about its circumference, such as no net torque applied to the tube.

According to another aspect of the invention, a method of restraint suited for determining the properties of a material based on a reaction to an external loading includes the steps of: (i) providing a test base including a moving drive and a stationary post, and a platform, test bed, hollow cylindrical tube having ends and being substantially formed by the material and first and second members adapted for gripping the respective tube ends; (ii) securing one end of the hollow cylindrical tube to the first member; (iii) connecting the platform to the drive; (iv) placing the test bed over the drive and platform; (v) connecting the first member to the test bed; (vi) after step (v), connecting the second member to the platform such that the second member is positioned above the test bed; and (vii) after step (vi), securing the other end of the tube to the second member.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIGS. 1A and 1B are schematic illustrations of a fixture for applying a tensile loading on a hollow cylindrical tube using a DMA. FIG. 1A shows the fixture and tube prior to moving a drive relative to a stationary post. FIG. 1B shows an elongation of the tube after the drive has moved relative to the post.

FIGS. 2A and 2B are schematic illustrations of a fixture for applying a transverse or bending load on a hollow cylindrical tube using a DMA. FIG. 2A shows the fixture and tube prior to moving a drive relative to a stationary post. FIG. 2B shows an elongation of the tube after the drive has moved relative to the post.

DETAILED DESCRIPTION OF THE INVENTION

Figure 3:
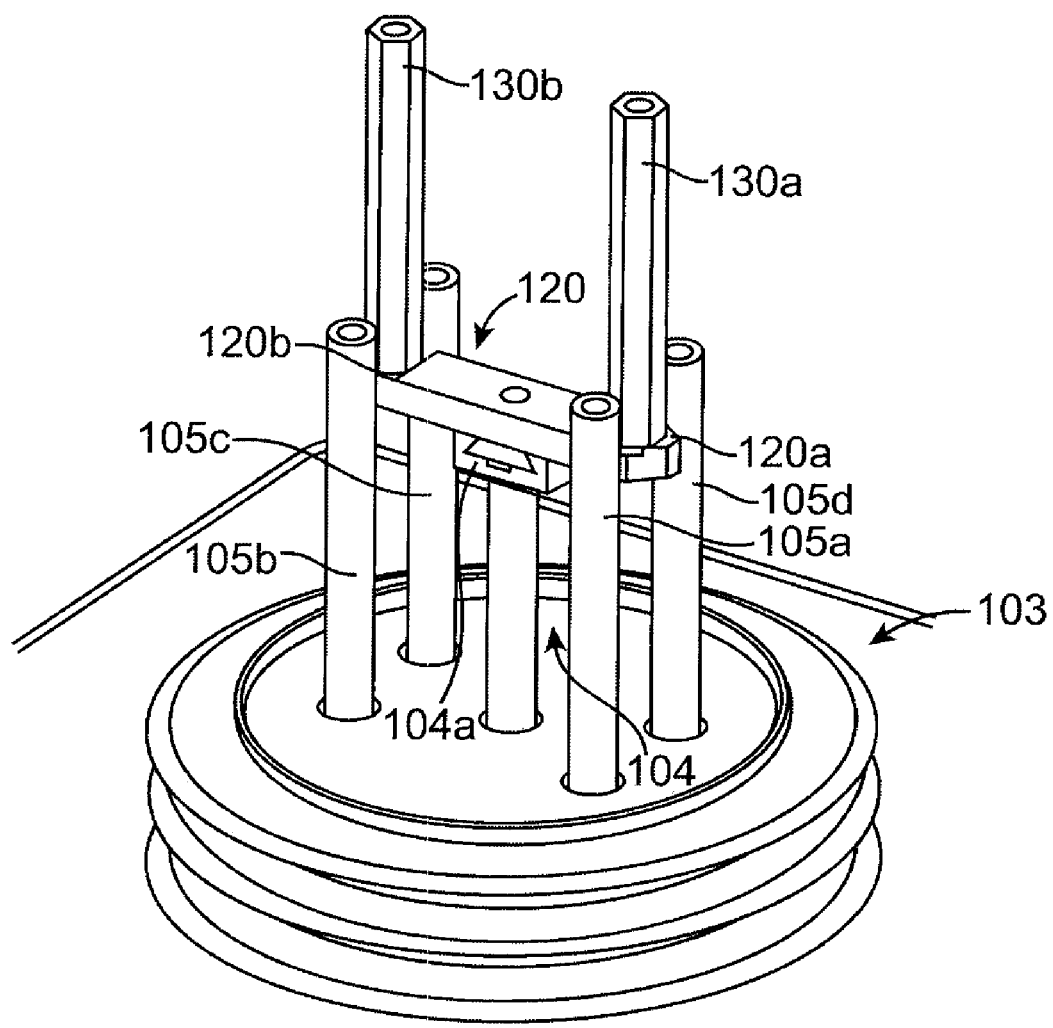
FIG. 3 shows a perspective view of a portion of a DMA with a first stage assembly of a fixture for performing a mechanical analysis of a hollow cylindrical tube. This first partial assembly may be used to construct a fixture for performing either a tensile or transverse load test on the tube. The portions of the DMA include a base, drive and stationary posts.

The description proceeds as follows. First, various aspects of fixtures according to the disclosure will be described with reference to FIGS. 1-2, which are psuedo-schematic representations of test fixtures according to the disclosure. These illustrations and accompanying text are intended to provide a simplification of the coupling loads between and/or among structure. Specifically, the drawings are intended to illustrate in accordance with the disclosure load paths for equilibrating loads carried by a structure during a test of a hollow cylindrical tube, in terms of a moving and stationary of a testing apparatus, e.g., a DMA, for wet (immersion) testing or dry testing of the hollow tube. Following this description, the discussion turns to a description of more specific examples of structure, namely, two embodiments of test fixtures described with reference to FIGS. 1 and 2. Examples of embodiments of more specific structure are discussed with reference to FIGS. 3-13.

Test Fixtures 1 and 2

FIGS. 1A and 2A are schematic representations of two embodiments of a test fixture 1 and 2, respectively, secured to a test bench 3 that provides a moving rod 4 (or drive assembly) and posts to mount a fixture. As alluded to above, these drawings are not intended to illustrate or even suggest actual dimensions or relative sizes of parts for a fixture according to the disclosure. Rather, as will be appreciated, they represent only a simplification of the load paths that are provided between the rod 4 and the posts 5. The components of the fixtures depicted in FIGS. 1 and 2 may, therefore, be considered as rigid bodies during the following discussion.

The first test fixture 1 is configured for restraining a wet or dry test sample (TS), i.e., a hollow cylindrical tube, when subjected at an axial load. The second test fixture 2 is configured for restraining the wet or dry TS when subjected to a transverse or bending load when both ends 11a, 11b of the tube are fixed in rotation (i.e., the slope at each end is unchanged when the TS is loaded). Other idealized boundary conditions for testing a hollow cylindrical tube, e.g., cantilever, dual cantilever, pinned at both ends, etc. become possible as well in view of this disclosure. FIGS. 1B and 2B show respective deformed states for the TS for each of the loading conditions. In some embodiments, parts may be common to both the fixture 1 and the fixture 2 as discussed in greater detail, below.

Test bench 3 may correspond to the test bench or chamber described in U.S. Pat. No. 5,710,426 (Reed). Bench 3 includes stationary or nonmoving posts 5a, 5b surrounding a rod 4 that is coupled to a drive mechanism (not shown) which displaces the rod 4 linearly. Examples of posts 5 and rod 4 are post 16 and drive rod 14, respectively, described in Reed. Rod 4 is part of a linear actuator configured to apply a predetermined static or time-varying (i.e., dynamic) displacement 6, which results in the deformed test specimen (TS') depicted in FIGS. 1B (axial deformation) and 2B (transverse deflection). Mechanical properties of material represented in TS when the TS is subjected to a static load, dynamic, i.e., time-varying load, and/or thermal loading can then be measured or predicted in terms of, e.g., measuring resistance forces in response to an enforced displacement. Thus, bench 3 may be enclosed within a thermal isolation chamber and may include appropriate instrumentation to measure forces acting on the rod 4.

Test fixtures 1 and 2 each include a pair of mount assemblies, namely, 12a and 12b, and 14a and 14b. Mount assembles 12a, 14a are coupled to the drive rod 4, while mount assemblies 12b/14b are coupled to the stationary posts 5. Mount assembles 12a/14a may include a beam 20, standoffs 30a and 30b, a top plate 50 and an upper clamp 40. Mount assemblies 12b/14b may include a platform 60 and a lower clamp 80.

Mount assemblies 12a/14a are coupled to the end of the rod 4 by way of a connecting portion of the beam 20, e.g., a dovetail fitting 4a. Standoffs 30a, 30b may be secured at their lower ends by removable fasteners, e.g., screws, to ends 20a, 20b of beam 20. The upper ends of the standoffs 30a, 30b support the plate 50, which may be secured to the standoffs 30a, 30b at its ends 50a, 50b, respectively, by removable fasteners. The clamp 40 may be affixed to the top plate 50 by removable fasteners. The clamp 40 is orientated to face downward so that a lower end 11a of TS faces the rod 4. In the case of test fixture 1 (tensile test), the clamp 40 is located on the plate 50 such that when the TS is secured to the clamp 40, the TS center axis falls on or near the line of action of the rod 4. The term "line of action" or LOA refers to the straight line that a force acts along. If the equilibrating force is located on this LOA then no equilibrating moment is needed. Thus, by locating the restraining force for end 11a along the rod 4 LOA this will ensure that the external, equilibrium forces acting on the TS, i.e., external forces acting on the TS free body, during the test are limited to axial loads as desired for a tensile axial load test. In the case of test fixture 2 the location of, e.g., the removable fastener that secures the clamp 40 to the plate 50 may fall on or near the LOA of the rod 4. In this case, the bending moments induced at end 11a are limited to only the one plane.

Mount assemblies 12b/14b are coupled to the stationary posts 5a, 5b, by way of, e.g., removable fasteners connecting ends 60a, 60b of the platform 60 to the upper ends of the posts as shown. Platform 60 provides support for the lower clamp 80 when the rod 4 is displaced upwards (FIG. 1B/2B) or downwards and may be formed to hold a volume of fluid in which the TS is immersed during testing. As indicated in FIG. 1, platform 60 also provides passageways 62a and 62b for standoffs 30a, 30b. This passageway may be formed as, e.g., through holes slightly larger than the cross-sectional dimensions of standoffs 30. In any event, the passageways 62a/62b permit unhindered displacement of the standoffs 30 relative to the platform 60. As such, with TS removed, the mount assembly 12a/14a can move freely up/down relative to the mount assembly 12b/14b (bearings or bushings may be provided to allow free travel within the passageways 62a/62b, especially in the case where a transverse load is applied to the TS). With this arrangement, the only structure that couples mount assembly 12a/14a (beam 20, standoffs 30, clamp 40 and plate 50) to mount assembly 12b/14b (frame 60 and clamp 80) is TS.

A travel distance or upwards/vertical clearance of "h" is created between the top of the beam 20 and bottom of the frame 60 when the unloaded test specimen is secured in place in the fixture, i.e., when TS is attached to clamps 40 and 80 as shown in FIGS. 1a and 2a. This distance h may represent the maximum amount of deflection δ by rod 4 permitted before beam 20 abuts the lower surface of the frame 60. FIGS. 1 and 2, showing exaggerated views of TS', depict the relationship between the deflection and movement of parts of the fixture relative to each other.

In comparing the locations of clamps 80 and 40 between mount assemblies 12a and 14a, the lower clamp (80) is situated to face left-to-right, and the upper clamp 40 right-to-left in frame 60 for a transverse loading, and up/down for a tensile loading. Assembly of the fixture 1 may proceed by securing the TS in the lower clamp 80 first, securing the plate 60 and then securing the end 11a to clamp 40. For the fixture 2, the TS may be attached to clamp 40 then to clamp 80 (as described in greater detail, below).

Test Fixture 100 (Tensile Test)

FIGS. 3-7 illustrate various partial assembly views of a test fixture 100 and components thereof that embody features of test fixture 1 just described with reference to FIGS. 1A-1B. Test fixture 100 includes a first and second mount assembly. The first mount assembly includes a beam 120, spacers 130a, 130b, top plate 150 and top clamp 140. The first mount assembly for fixture 100 embodies features of the first mount assembly 12a discussed earlier in connection with FIG. 1A. The second mount assembly includes a platform 160 (formed by a frame 162 and bed 164), and a lower clamp 180. The second mount assembly for fixture 100 embodies features of the second mount assembly 12b discussed earlier in connection with FIG. 1A.

Figure 7A:
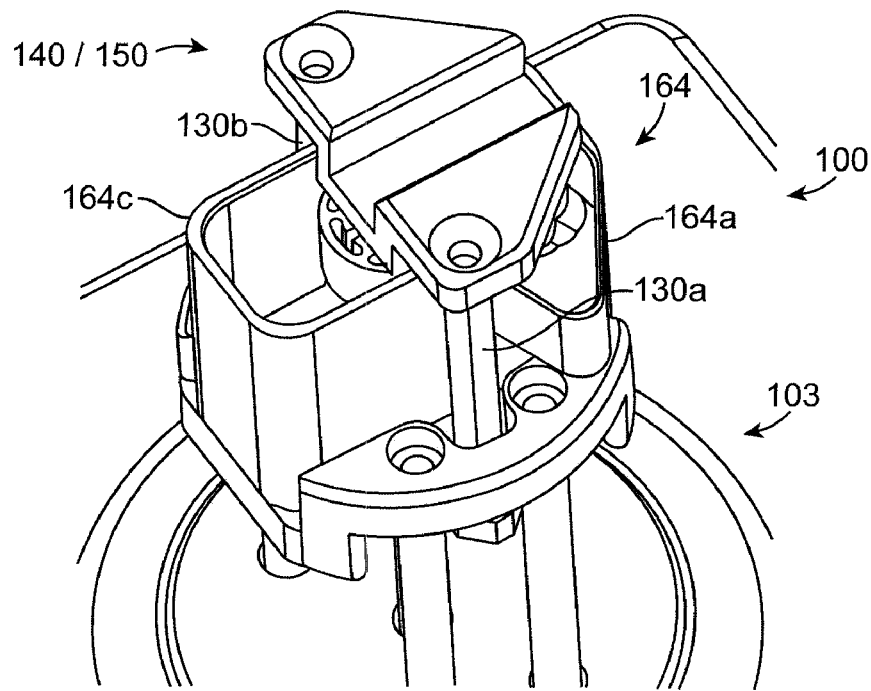
FIGS. 7A and 7B show perspective views of the assembled fixture for performing a tensile load test on the tube.

FIG. 3 illustrate a first step of assembly for the test fixture 100. This is a perspective view of a test base 103 with the beam 120 and spacers 130a, 130b (tensile load) attached to ends 120a, 120b, respectively, by fasteners, e.g., screws. The beam 120 is secured to the top of the drive rod 104 by a dovetail connection 104a (may also include tightening a dome-top set screw which connects the beam 120 directly to the dovetail head formed at the end of the rod 104). There are four stationary posts 105a, 105b, 105c and 105d surrounding the drive rod 104. The base 103 is located within a thermal isolation chamber of a DMA, e.g., the TA Instruments, Inc. "Q800 DMA" described online at http://www.tainstruments.com/product.aspx?n=1&id=12&siteid=11. The spacers 130a, 130b are tapped at their upper ends, which is where they will attach to the clamp assembly (clamp 140, plate 150) as depicted in FIG. 7A.

Figure 4A:
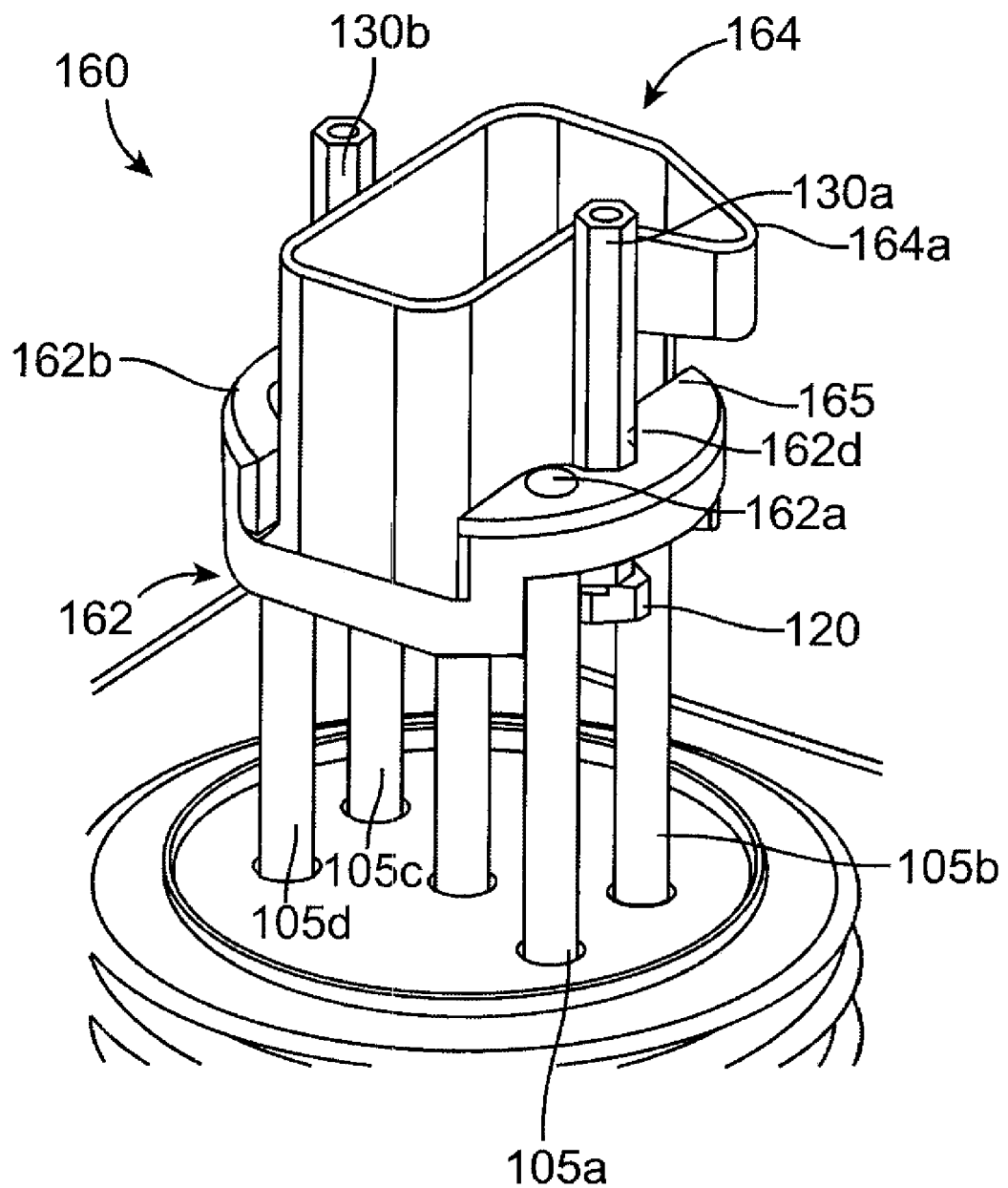
FIGS. 4A and 4B show perspective views of a second stage of assembly of a fixture for performing a tensile load test of the tube after the first stage.
Figure 4B:
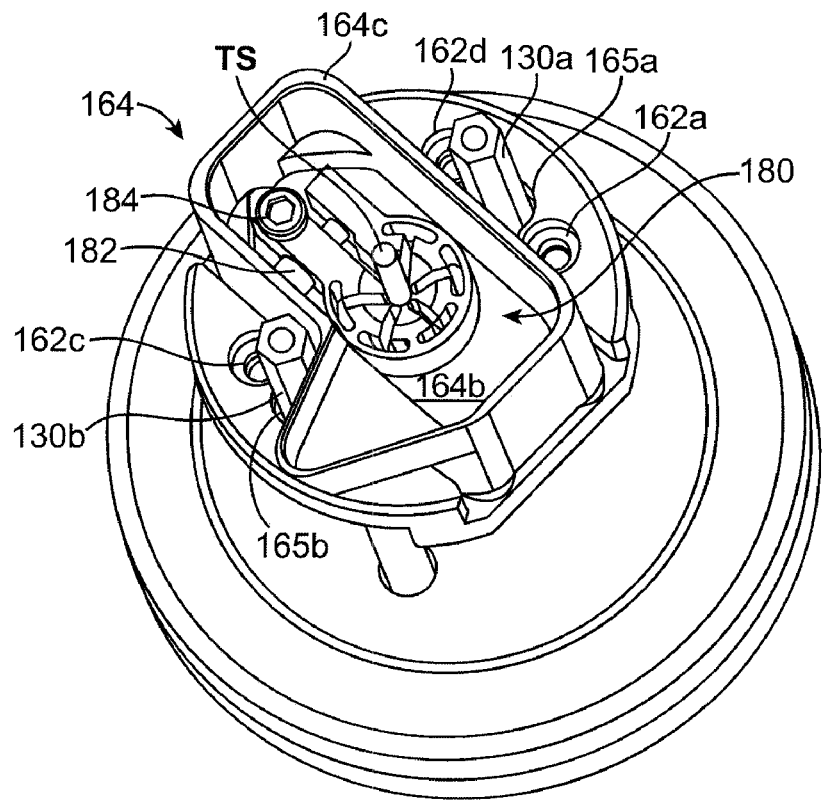
Figure 7B:
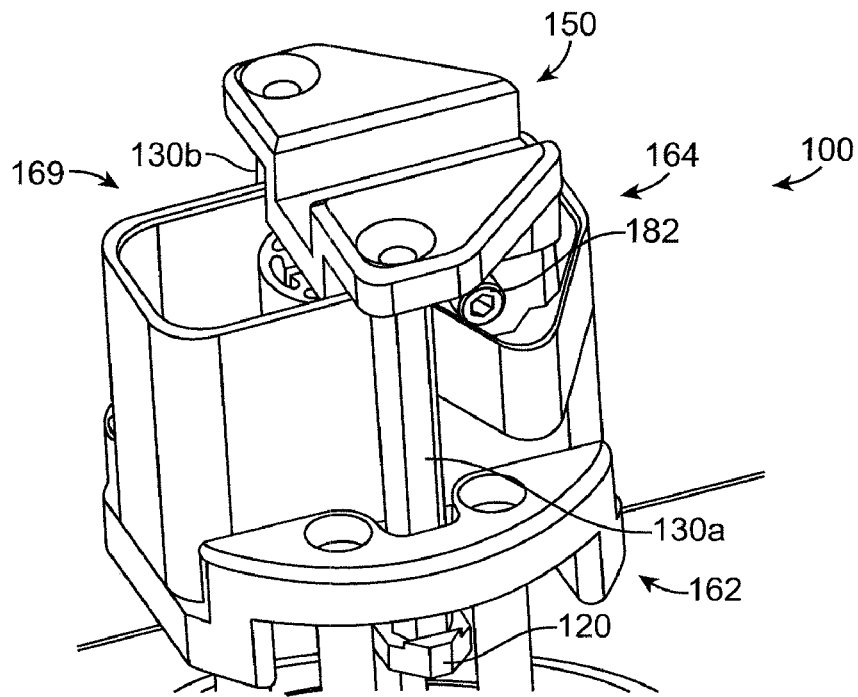

FIGS. 4A-4B illustrate a second step of assembly for the test fixture 100. According to this embodiment the test platform 160 is formed by a frame 162 supporting a bed 164. The frame 162 includes four bores which align with the tapped upper ends of the posts 105a, 105b, 105c, 105d. The frame 162 may be secured to the bed 164 prior to securing it to the posts 105. The lower surface of the frame 162 is disposed above the upper surface of the beam 120 when the fixture is fully assembled (FIG. 7B). The platform 160 may be suspended from the posts 105 and thus rest above the beam 120 so that the beam 120 can be moved upwards, thereby causing elongation of the TS without abutting the lower surface of the frame 162.

The bed 164 is formed with walls 164c and a base 164b which together define a volume for a liquid in which a TS can be immersed during testing. A material immersed in a liquid can exhibit different mechanical properties, e.g., glass transition temperature ($T_g$), then when its properties are measured in air. In some embodiments a tensile or bending test is conducted with the TS immersed in a liquid, such as a PBS buffer. The bed 164 includes an access 164a for accessing a tightening screw for the upper clamp 140 (FIG. 7B). In other embodiments, the bed 164 may have more shallow walls, or a bed may not be used at all if the TS is loaded in air (as opposed to immersion testing). The bed 164 may be structural or non-structural with respect to load transfer from the clamp 180 (by TS when in tension) to the stationary posts 105. A structural embodiment may have the clamp 180 and TS secured to the base 164b portion of the bed 164 and the bed 164 attached separately to the frame 162. A non-structural embodiment (preferred) of the bed 164 may have the clamp 180 secured directly to the frame 162, i.e., the fastener 184 portion of the clamp 180 attached directly to the frame 162, while the bed base 164b is disposed between the frame 162 and the clamp 180.

Figure 5:
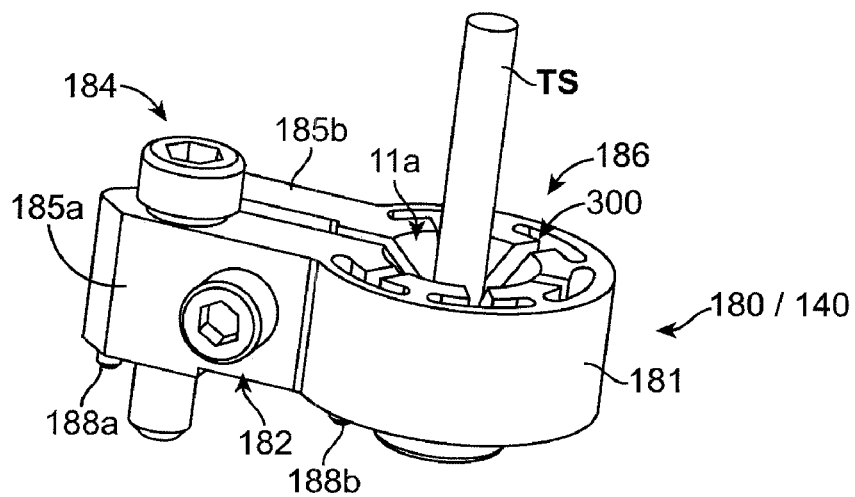
FIG. 5 shows a perspective view of a first clamp assembly with one end of the hollowing cylindrical tube (TS) secured in the clamp.

The clamp 180 is shown in perspective view in FIG. 5 and secured to the frame 162 in FIG. 4B. As illustrated, the lower end 11a of the TS is received in an opening 186 and held therein by a plurality of fingers 300 formed along an annular portion 181 of the clamp 180. In some embodiments, the fingers 300 have a design such that little or no net torque is applied to the TS when the fingers 300 are pressed into the TS (examples of fingers 300 are discussed in greater detail, below). The pressure applied to the TS by the fingers 300 is controlled by a fastener 182, e.g., a hex-head screw, which connects two opposing arms 185a, 185b. These arms extend from the annular portion 181. When the arms 185 are brought together, e.g., by turning the fastener 182 clockwise, the fingers 300 bear down upon the lower end 11a of the TS. When the arms 185a, 185b are moved apart, e.g., removing the fastener 182, the pressure on the lower end 11a is relieved and the TS can be removed.

Referring to FIG. 5, as a part of the step 2 assembly the TS is placed within the clamp 180 and secured thereto using the fastener 182 (FIG. 5) before the clamp 180 is secured within the bed 162. The clamp 180 may include pins and/or set screws extending from its base, 188a and 188b, as shown in FIG. 5, which are received within corresponding slots, holes or depressions formed in the base 164 (hidden from view in FIG. 4B). As will be appreciated, the pins 188 cooperate with the fastener 182 to close the clamp 180/140 (pins 188 hold one of the clamp arms in place when the screw 182 is turned clockwise). According to some embodiments, the entire tensile load transferred through the TS during testing is carried in bending and tension through the fastener 184. After the TS end 11a is secured in the clamp 180, the clamp 180 is secured to the frame 162 by extending the fastener 184 through a hole formed in the base of the bed 164.

Step 2 of the assembly for fixture 100 may proceed as follows: secure the bed 164 to the frame 162, secure the frame 162 to the posts 105, connect the lower end 11a of the TS to the clamp 180, place the set screws 188 in the holes/slots provided in the bed 164b, and then secure the clamp 180 in the frame 162. After completing Step 2, the upper clamp pieces, i.e., clamp 140 and plate 150, are assembled.

Figure 6A:
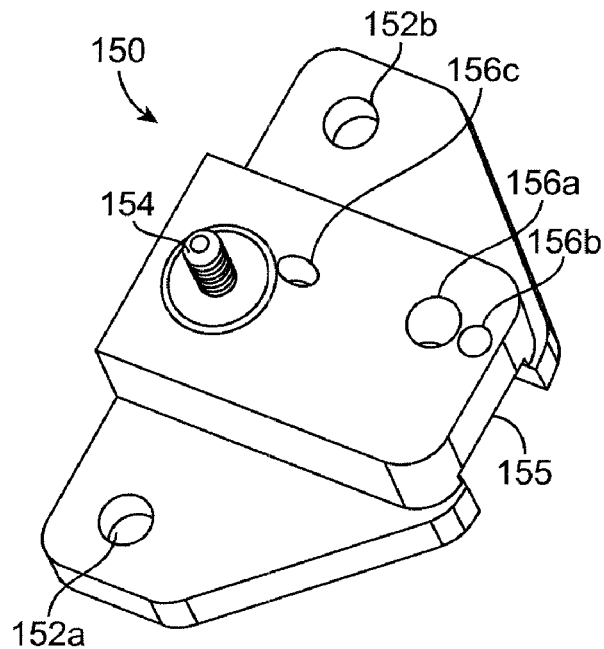
FIG. 6A shows a plate for holding a second clamp.
Figure 6B:
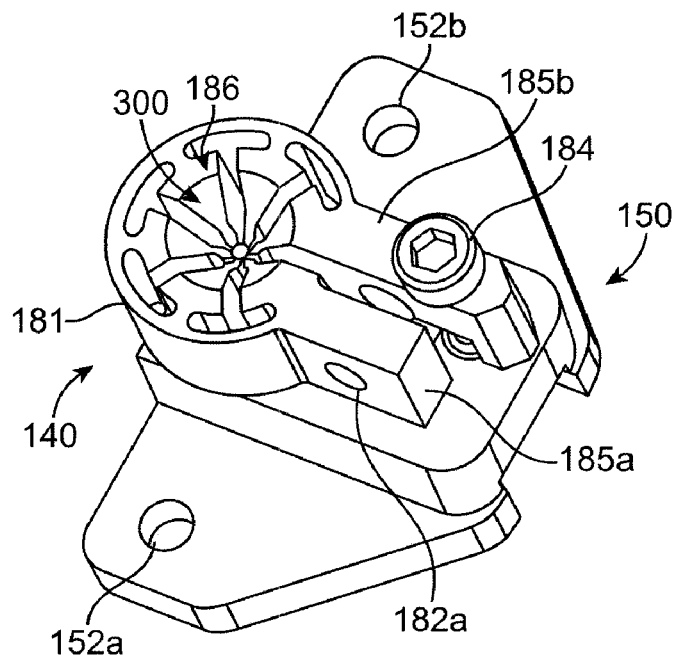
FIG. 6B shows the assembly of the plate of FIG. 6A and the second clamp.

FIGS. 6A-6B show structure for the clamp 140 and the plate 150. FIG. 6A shows the plate 150 only and FIG. 6B shows the plate 150 with the clamp 140 secured thereto. For some embodiments, e.g., the illustrated embodiment, the clamp 140 may be identical to the clamp 180 just described. In other embodiments, the clamps 140 and 180 may be different. For example, the location of fastening or set screws, e.g., pins, for the clamp 180 may be different from clamp 140 in order to provide more convenient access points for assembly of the fixture 100.

In the illustrated embodiment the clamp 140 is identical to the lower clamp (clamp 180). Accordingly, the same reference numerals will be used to refer structure when the structure is the same. Referring to FIG. 6A, the perspective view shows the face of the plate 150 that faces the base 164b of the bed 164 (FIG. 7A shows the opposing face of the plate 150). The plate 150 includes a tapped hole 156a that receives the captive screw 184, and two slots that receives the pins 188, 188b. Bores 152a, 152b align with the top of the spacers 130a, 130b to secure the plate 150 to the spacers 130. The plate 150 includes a central portion 155 that is sized to fit into the opening of the bed 164 (see FIG. 7A) for purposes of alignment of the bores 152a, 152b with the top of the spacers 130. The central portion 154 includes a peg 154 that is received within the bore of the upper end 11b of the TS. The peg 154 aligns with the center of the opening 186 of the clamp 140 when the clamp 140 is fit onto the plate 150. Thus, when the TS upper end 11b is received in the opening 186, it will be placed between the contacting surfaces of the fingers 300 (discussed below) and the peg 154. The assembled view of the upper clamp assembly is shown in FIG. 6B, which also shows the opening 182a in the arms 185 for the tightening screw. The tightening screw 182 is used to secure the end 11a of the TS after the plate 150 has been secured to the top of the spacers 130.

After the plate 150 and clamp 140 have been assembled (FIG. 6B), the rod 104 of the base 103 is moved to the top of its travel and locked in place. After the arm 104 has been locked in place, the plate 150 is connected to the top of the spacers 130 by threaded fasteners that are passed through the bores 152a, 152b of the plate 150, as shown in FIG. 7A. As the plate is being placed onto the spacers 130, the end 11b of the TS central axis should be aligned with the opening 186 of the clamp 140. After the plate 150 is secured in place, the rod 104 is unlocked and the end 11b is allowed to pass into the opening of the clamp 186 as the rod 104 moves downward towards the base 103. The end 11b of the TS may abut the base of the peg 154. After this step, the tightening fastener 182 is inserted into the opening 182b and turned to cause the fingers 300 to grip the upper end 11b of the TS (in one example, the TS (i.e., a hollow cylindrical tube) has a length of 1 inch (+/−0.05 inches)). Referring to FIG. 7B, the access opening 164a provided by the walls 164c of the bed 164 allows, e.g., a wrench, to be inserted between the walls 164c of the bed 164 and the plate 150 so that the fastener 182 and be tightened/loosened. After the assembly is complete (FIG. 7B), an opening 169 to the bed 164 may be used to fill the bed 164 with the liquid used to immerse the TS for an immersion testing of the TS.

Test Fixture 200 (Transverse Load Test)

FIGS. 8-11 illustrate various partial assembly views of a test fixture 200 configured for performing a transverse or bending test on the TS. The test fixture 200 and components thereof embody features of the test fixture 2 previously described with reference to FIGS. 2A-2B. Test fixture 200 includes a first and second mount assembly, which may share many of the same components as the first and second mount assembly used for test fixture 100. The shared components may include the beam 120, spacers 130a, 130b, frame 162 and clamps 140 and 180. The remaining components, i.e., the top plate and the bed differ between the fixture 100 and fixture 200. In the following description, the structure that is the same between fixture 100 and 200 will also use the same reference numerals.

The first mount assembly for fixture 200 embodies features of the first mount assembly 14a discussed earlier in connection with FIG. 2A. The first mount assembly includes the beam 120, the spacers 130, a top plate 150' and the top clamp 140. The second mount assembly for fixture 200 embodies features of the second mount assembly 14b discussed earlier in connection with FIG. 2A. The second mount assembly includes a platform 160' (formed by the frame 162 and bed 164'), and the lower clamp 180.

Step 1 of the fixture 200 assembly is the same as before, i.e., secure the beam 120 and spacers 130 to the test base 103.

Figure 8:
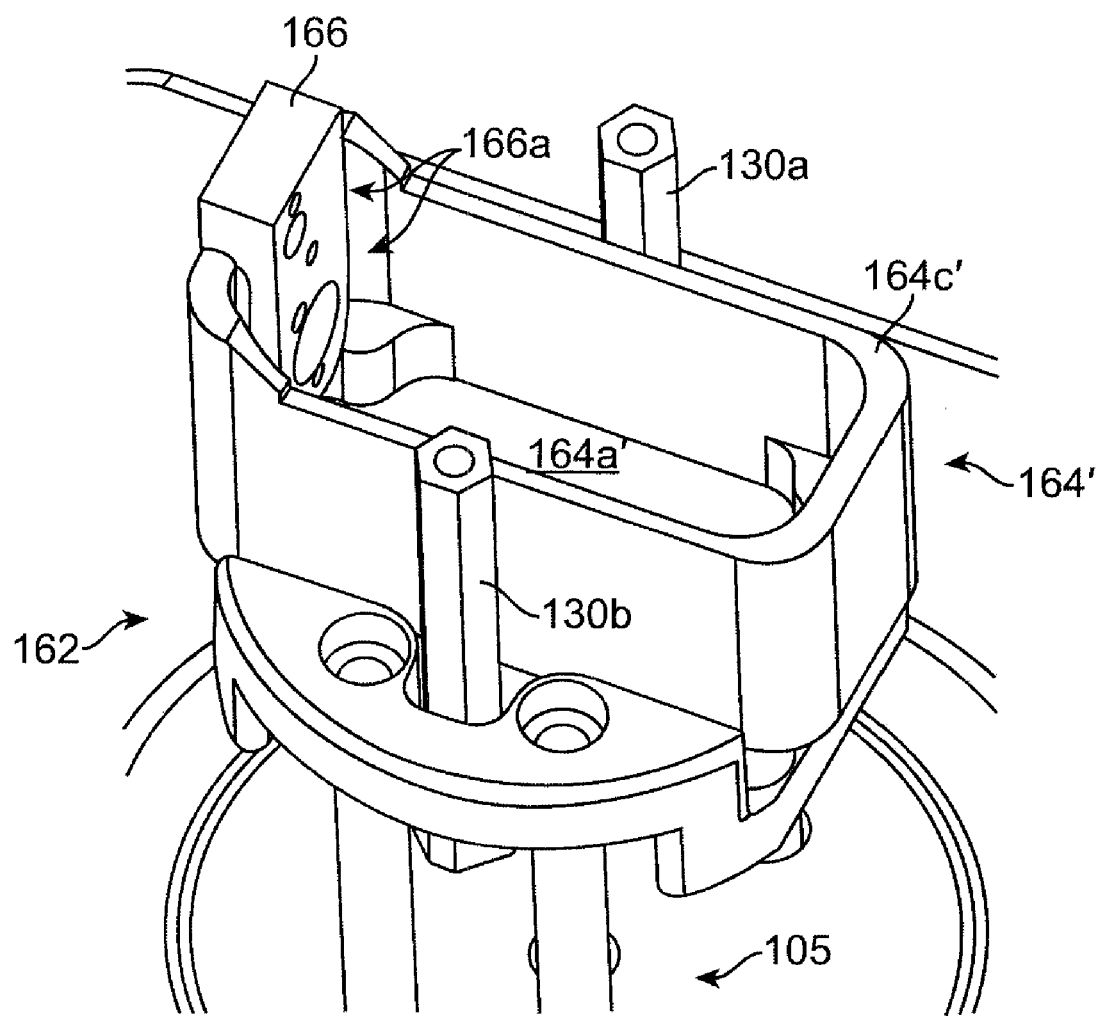
FIG. 8 shows a perspective view of a second stage of assembly of a fixture for performing a transverse or bending load test of the tube after the first stage of FIG. 3.

Step 2 is depicted in FIG. 8. The frame 162 and a bed 164' are secured to the base 130 in similar fashion as described earlier in connection with platform 160. In the case of fixture 200, the bed 164' takes on a different form from bed 164 since the TS will be loaded by a traverse loading. Bracket 166, having mounting holes 166a for securing clamp 180 thereto (as before), is attached at a wall of the bed 164'. The mounting holes 166a are arranged so that the opening 186 of the clamp (for receiving an end of the TS) will face left to right (as opposed to bottom to top).

Figure 9:
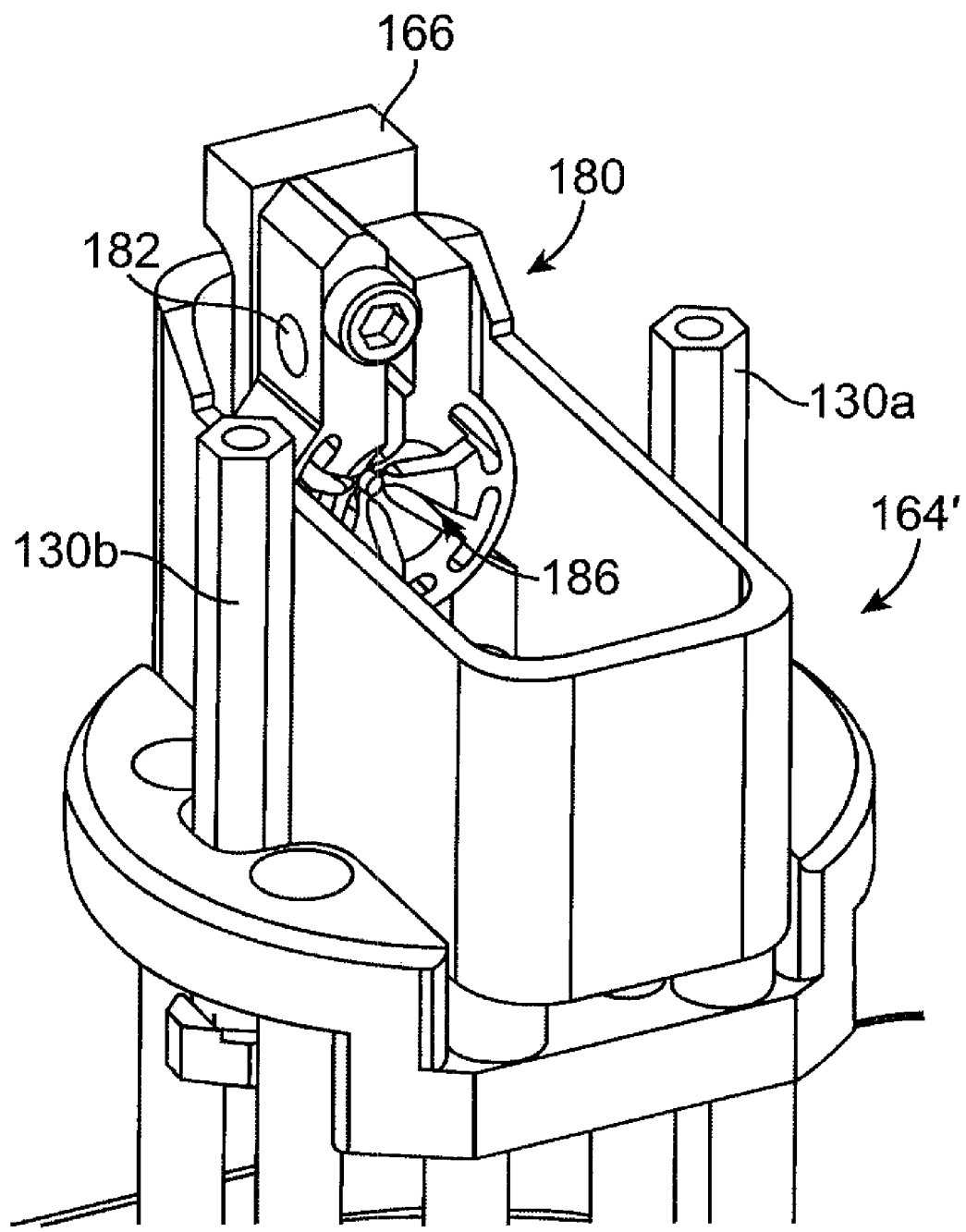
FIG. 9 shows a perspective view of a third second stage of assembly of a fixture for performing a transverse or bending load test of the tube after the first stage of FIG. 3.

Step 2 of the fixture 200 assembly is illustrated in FIG. 9. In this step the clamp 180 is attached to the bracket 166. In contrast to fixture 100, the TS is not secured in the clamp 180 at this point. Rather the TS is attached to the upper clamp 140 first, then to the lower clamp 180 during the final assembly. As can be appreciated from inspection of FIG. 9, the bed 164', bracket 166 and/or clamp 140 may cooperate so that the hole 182a for receiving the tightening fastener 182 can be easily accessed after the top plate and clamp assembly (described next) are attached to the tops of the spacers 130.

Figure 10A:
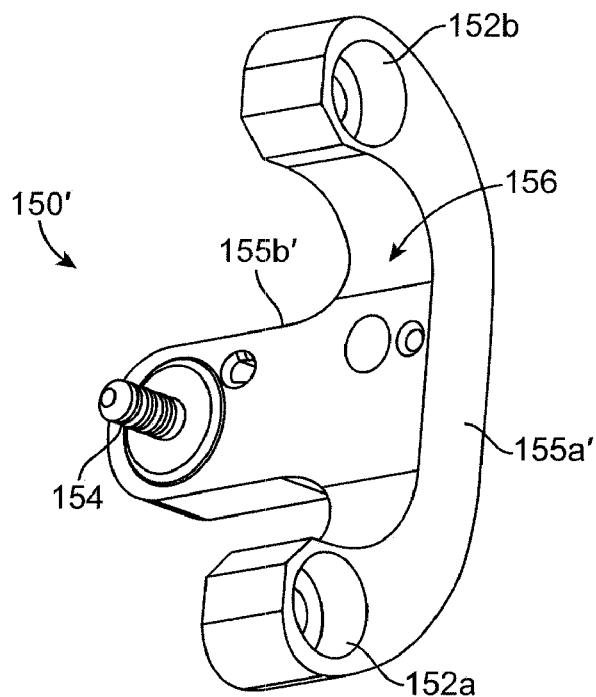
FIG. 10A shows a plate for holding a clamp.
Figure 10B:
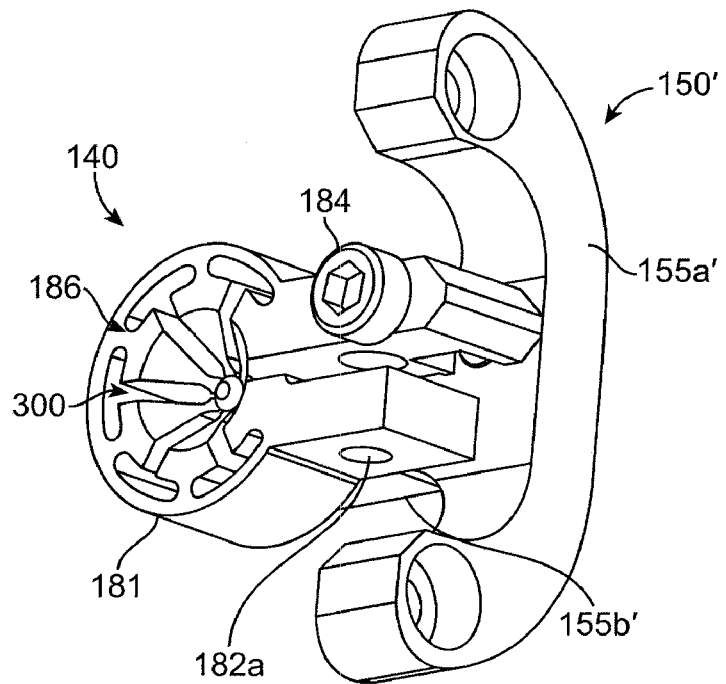
FIG. 10B shows the assembly of the plate of FIG. 10A and the clamp.
Figure 10C:
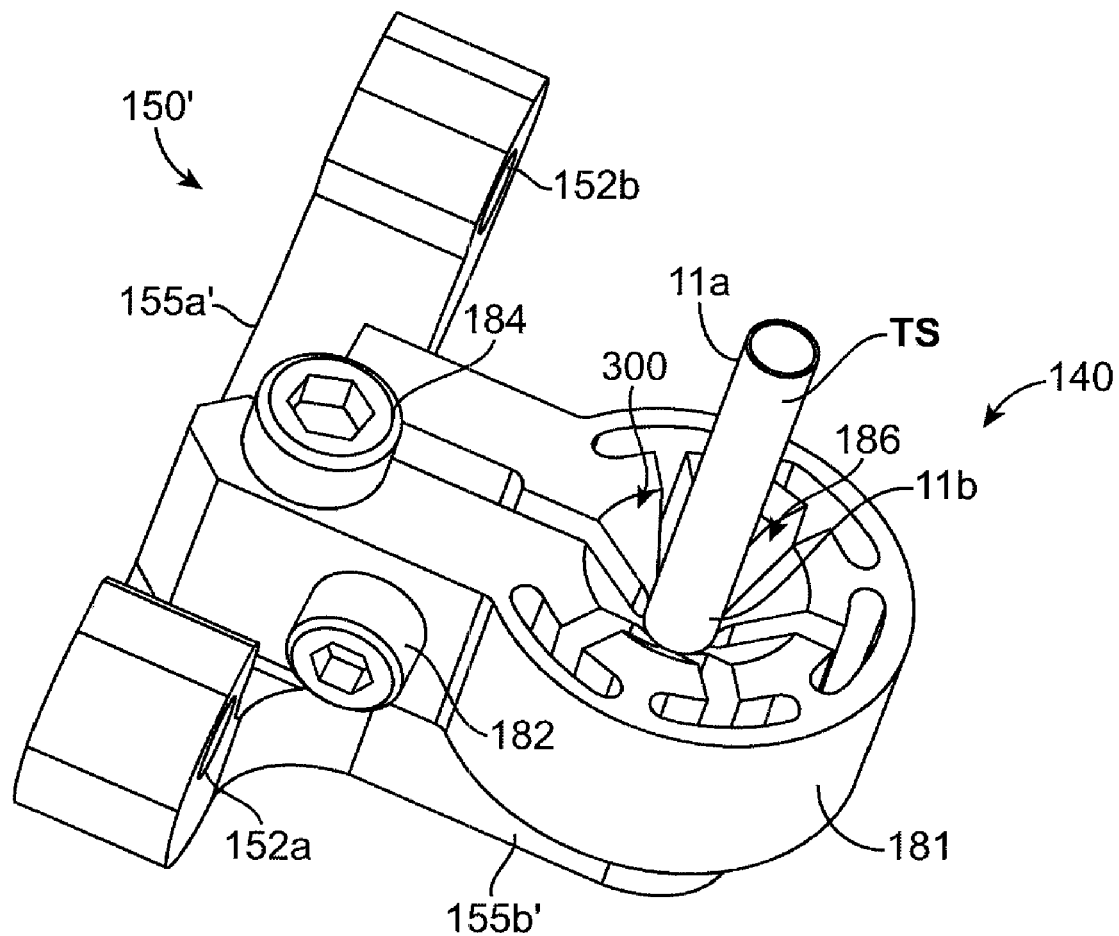
FIG. 10C shows the tube secured to the clamp and plate of FIG. 10B.

Step 3 of the fixture 200 assembly is illustrated in FIGS. 10A-10C. FIG. 10A illustrates a perspective view of a top plate 150'. In step 3 the clamp 140 is secured to the top plate 150' (FIG. 10B) then the TS upper end 11b is secured in the clamp 140 (FIG. 10C). Plate 150' includes an arched portion 155a' and an extension 155b'. Arched portion 155a' includes the bores 152a, 152b at the ends. The peg 154 (where the end 11b of the TS is received) is located at the end of the extension 155b'. The holes 156 for receiving the pins and the captive screw 184 are shown. The captive screw 184 is shown inserted into the extension 155b' in FIG. 10B. The location of the opening 186 and fingers 300 of the clamp 140 are depicted relative to the bores 152a and 152b. In this case, the opening 186 is located such that when the plate 150' is secured to the top of the spacers 130 the opening 186 associated with the lower clamp 180 will align with the TS held by the upper clamp 140, i.e., their centers lie on the same axis, so that no transverse pre-load is applied to the TS when end 11b is secured to clamp 140. Again, the arm 104 position may be adjusted (i.e., moved to the top of its travel) in order to locate this position of clamp 140 with respect to clamp 140.

Figure 11:
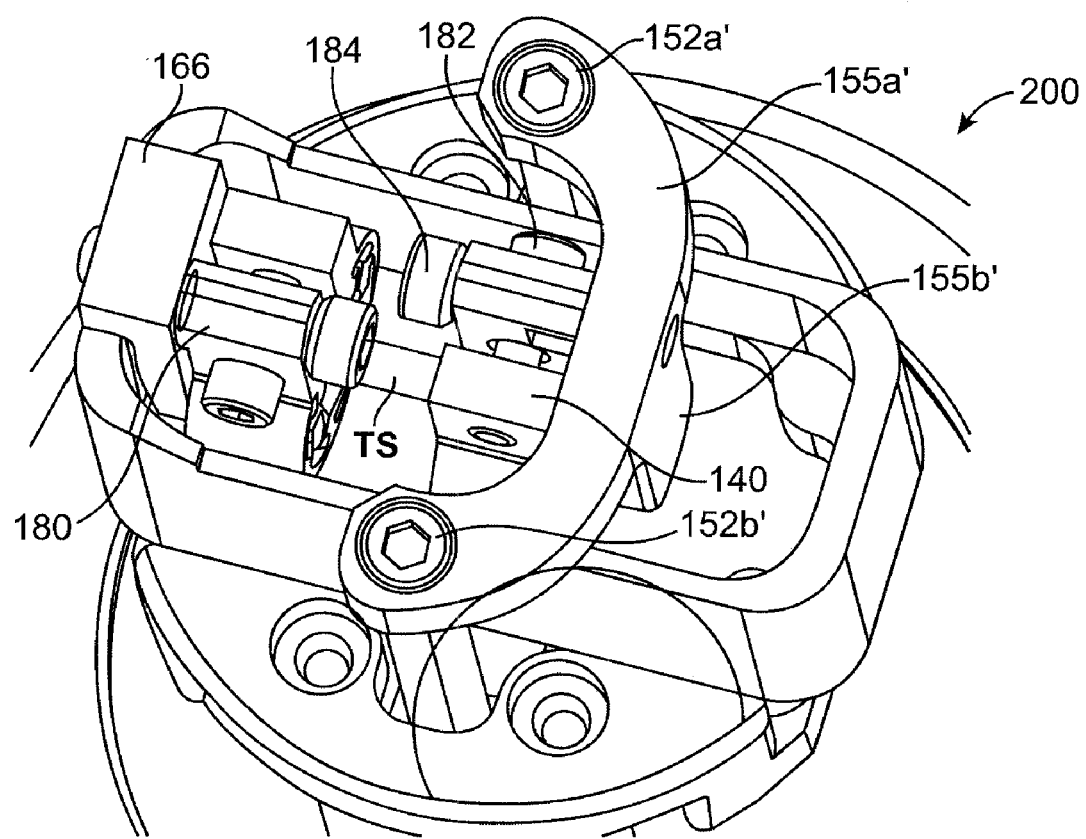
FIG. 11 shows a perspective view of the assembled fixture for performing a transverse or bending load test on the tube.

In step 4 of the fixture 200 assembly the top plate 150' and clamp 140 are secured to the spacers 130 using a fastener received in the bores 152a', 152b', as shown in FIG. 11, which shows a final assembly of the fixture 200. As can be appreciated from this top perspective view, the arched portion 155a' allows the clamp 140 (coupled to the drive 104) to be set back or recessed from the clamp 180 (coupled to the posts 105). This arrangement has at least one possible advantage. It allows the effective length of the TS to be greater, thereby allowing a test to be conducted on long beams, which means that more of a bending stress condition can be imposed on the TS, i.e., end loading a long slender beam, as opposed to shear stress condition, i.e., end loading a short and wide beam. Further, it enables a tube of a specific length, such as the intended length of a stent, to be examined.

Tube Clamp

The following discussion provides description of embodiments of a tube clamp according to another aspect of the disclosure. In particular, embodiments of the tube clamps 180/140 discussed below enable a hollow cylindrical tube, e.g., an extruded polymer tube having a 0.064" outer diameter (0.021" inner diameter) or 0.136" outer diameter (0.124" outer diameter), to be firmly held without crimping or buckling the ends, without applying a torque pre-load, and without requiring an excessive length of the tube to secure the clamping surfaces sufficient to prevent pull-out during testing. In other words, a relative small portion of the tube is clamped.

As will be appreciated, the effective length of the tube for purposes of calculating mechanical properties, e.g., under a bending stress condition, is the length between where the opposed clamps are in contact with the tube. One advantage of the design is that the length over which the clamp acts is not significant. Therefore, a greater percentage of the length of the tubing can correspond to the theoretical length of the tubing for purposes of calculating a flexural (EI) modulus or glass transition temperature ($T_g$). In one example the TS is 1" in length having the above diameters and received in a fixture 100/200 that is mounted within the test chamber of the Q800 DMA, or the DMA described in Reed. An additional concern is avoiding a torque pre-load, especially for thin-walled tubes.

Figure 12:
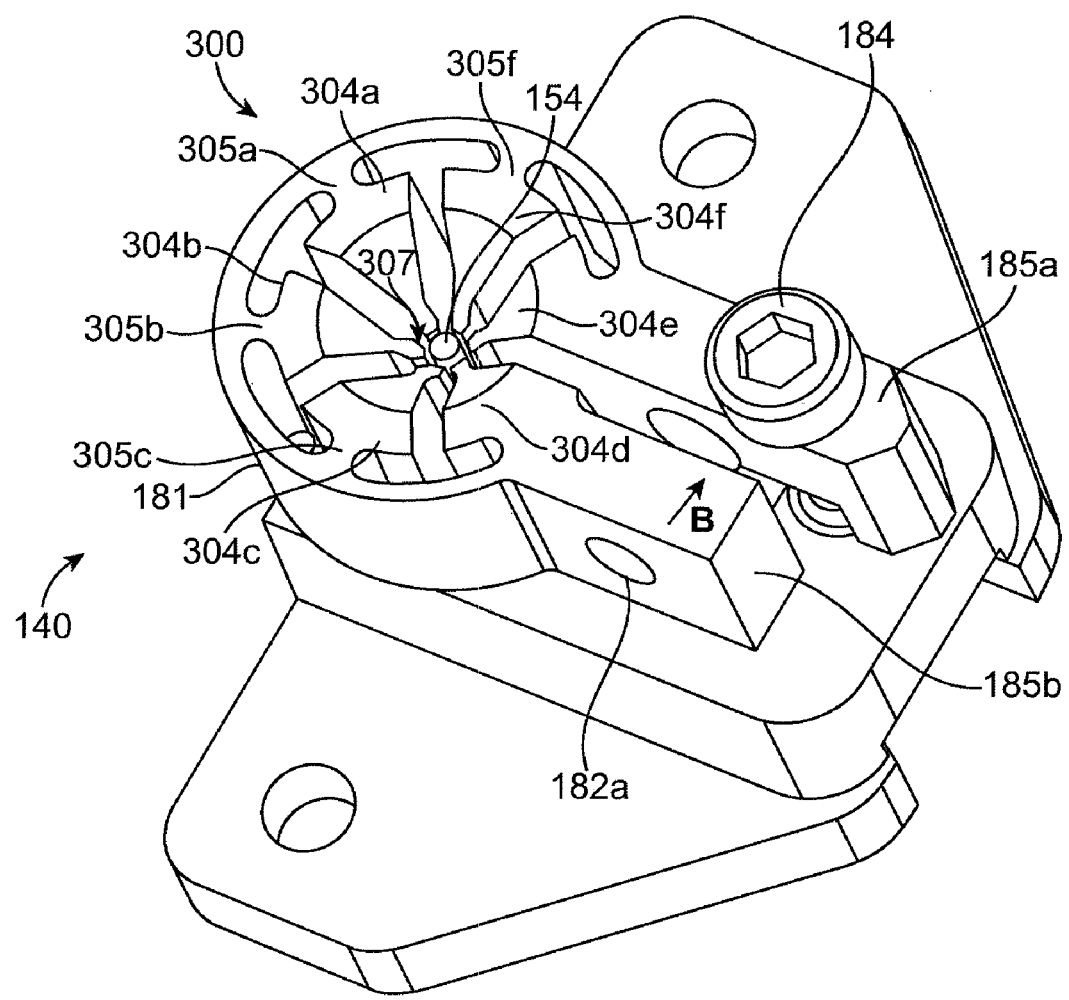
FIG. 12 shows a perspective view of the plate and clamp of FIG. 6B.
Figure 13:
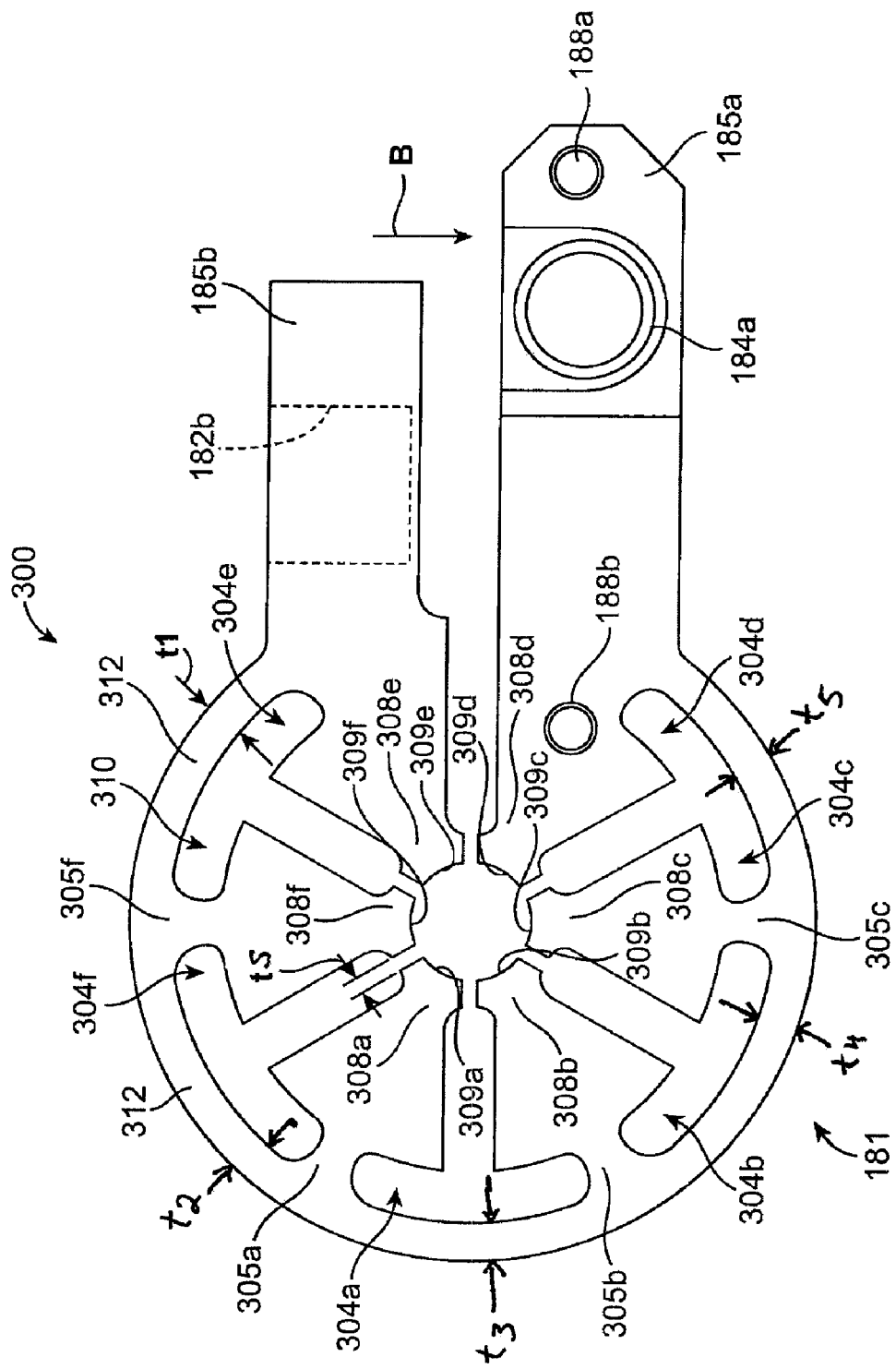
FIG. 13 shows a planar view of the clamp of FIG. 5.

Referring to FIGS. 12-13 depicted are embodiments of the tube clamp 180/140 described earlier. FIG. 12 shows a perspective view of the clamp 140/180 mounted on the upper plate 150' associated with fixture 200 (described earlier). With reference to FIGS. 12 and 13 depict one embodiment of clamping fingers 300, namely fingers 304 disposed angularly about a center of the clamp, i.e., where the peg 154 is located. For instance, fingers 304 may be used to grip an extruded polymer hollow cylindrical tube having a 0.064" outer diameter (0.021" inner diameter) or an extruded polymer hollow cylindrical tube having a 0.136" outer diameter (0.124" outer diameter).

As mentioned above, the upper end 11b of the TS is secured in the clamp 140 by placing the end 11b in the opening 186 such that the peg 154 passes into the bore of the TS and the walls of the TS are between bearing surfaces of the clamp 140 and the surfaces of the peg 154. The bearing surfaces of the clamp are indicated as surfaces 309 in FIG. 12. They are surrounding the outer surface of the peg 154. After the arm 185a has been secured to the plate 150' via the fastener 184, and with the pins or set screws 188 on the mating face portion of the arm 185a received in their matching holes 156 formed on the plate portion 155b' (as discussed earlier), the end 11b is inserted into the opening 186 such that the walls of the end 11b are between the peg 154 and the bearing surfaces 309. Once in position, the fastener 182 (not shown) is inserted into the hole 182a, e.g., by inserting the tip of the fastener 182 first into the portion of opening 182 formed on arm 185a. The tip of this fastener then engages the tapped hole 182a on the arm 185a. When so engaged and the screw 182 turned clockwise the engaging threads cause the arm 185b to be pulled towards the arm 185a (since the arm 185a is fixed in place by the set screws, it does not move). The rate at which the arm 185a is brought towards the arm 185b may be controlled by the pitch on the threads of the fastener 182. A higher or finer pitch can offer more control over the applied pressure as a function of the turning angle. A fastener having 32 threads per inch may be satisfactory to provide the desired amount of control over the clamp pressure and can provide an acceptable guarantee that the threads will not slip during testing, thereby possibly causing the TS to slip out of the clamp. A lockable fastener may be used to ensure the pressure applied to the TS during a test does not change. The desired amount of pressure to be applied to the TS may be controlled by using a tool in which the maximum torque applied to the fastener 182 can be controlled.

The foregoing action of the fastener 182 and arm 185b may thus close the bearing surfaces 309 down upon the outer surface of the end 11b of the TS, thereby clamping the TS. The direction of motion in which the arm 185a is drawn to close the clamp is indicated in FIGS. 12 and 13 by B and the structure described thereon. Referring briefly to FIG. 13, depicted are the locations of the set screws 188a, 188b relative to the hole 184a receiving the captive screw 184 and the tapped hole 182a that draws the arm 185b towards the arm 185a (thereby closing the clamp 140). From this drawing it will be appreciated that arm 185a is fixed in place (due to the set screws and captive screw) and as one observes the deflection of fingers (i.e., finger 304a through finger 304f) radially inward, it will be appreciated that the deflection inward increases as one moves clockwise in FIG. 13 from arm 185a towards arm 185b. This aspect of the clamp 140 will be described in greater detail shortly.

A peg 154 receivable in the TS's bore is preferred. Such an inner wall support can reduce chances of buckling of the piece when the surfaces 309 are brought down upon the TS, facilitate accurate mounting and allows greater pressure to be applied to the tube. The peg 154 may extend slightly forward of the ends of the bearing surfaces 309, as shown, and the peg 154 may have a chamfered end to make it easier to place a tube on the peg 154. In other embodiments the peg height may extend substantially further out from the ends of the surfaces 309 as this will further reduce instances of tube damage during assembly. Since such an embodiment may not be desirable for a transverse load test (since the extended length peg 154 can interfere with an intended deflection of the TS during testing). The extended peg embodiments may be preferred only for tensile load tests.

Referring now to FIG. 13 (a slice of the clamp 140/180 in a plane that is perpendicular to the longitudinal axis of the TS when received in the clamp), the clamp 140 is capable of applying a uniform radially inward pressure to the outer surface of the end 11b when received within the circle of bearing surfaces 309 depicted in FIG. 13. The clamp 140 structure is also capable of applying a pressure to the outer surface of a hollow cylindrical tube without a significant net torque applied to the tube as the arm 185b is pulled towards the arm 185a. Such a requirement may be particularly important for an extruded polymer hollow tube of material of small dimensions, see e.g. examples of dimensions above, which are used to construct medical device because when there is a torsional preload (caused by the clamp) the resulting measured/computed mechanical properties (which typically assume no such preload is present in the material) will be inaccurate. For a solid tube the effects of torsion may not warrant a concern over a torsional preload applied by the clamp, as is known in the art. However, when a hollow tube with relatively thin walls is being tested, e.g., a stent tube, the effects of a torsional preload can be significant.

There may be six, less than six, or more than six fingers 304 provided on the clamp 140. The clamp 140 may exhibit the following stiffness properties, which will generally be described in terms of polar coordinates where the Z axis is out of plane, radial (r) and angular (A) are the in-plane radial and angular components of movement with origin at the center of the clamping area (i.e., where the end 11 of the TS is placed). The clamp is formed as an annular body 181 in which the arms 185 extend out from the open end (as discussed earlier). The clamp includes a ring 312 connecting the arm 185a to the arm 185b. The ring 312 thickness is much less than the arm thickness 185a and thus the ring 312 is flexible in terms of radial deflection compared with the arms 185. Located inside of the ring 312 are six fingers 304a, 304b, 304c, 304d, 304e and 304f. Each finger includes a tip 308a, 308b, 308c, 308d, 308e and 308f that forms the bearing surfaces 309a, 309b, 309c, 309d, 309e and 309f. Collectively, the bearing surfaces describe an arc length that extends approximate 360 degrees. Between each bearing surface 309 there is a spacing ta. When the clamp 140 is brought down upon the TS the space ta vanishes and the bearing surfaces 309 come together to form an essentially 360 degree contiguous bearing surface that retains the TS end in the clamp by the application of a 360 degree uniform pressure to the outer surface of the TS.

The foregoing deformation of the clamp structure when clamped to the TS is such that a minimal net torque exists on the end 11 when the tips 308 come together. This result may be achieved by varying the thickness of the ring 312 sections, e.g., the section extending between portions 305f and 305a and having a thickness t2, the section extending between portions 305f and 305a and having a thickness t3, which is different from t2, etc. (see FIG. 13). By varying the thickness, the stiffness of these ring sections can be increased or decreased relative to the each other, which produces a corresponding redistribution of the load about the clamp and applied to the TS through the bearing surfaces 309 of the fingers 304. Thus, t1 can be modified relative to t2 (e.g., the average thickness of t1 decreased relative to the average thickness of t2) to effect the percentage of the total load applied by 308e or 308f, t2 can be modified relative to t3 and t1 to equalize the contributions to the total load originating from each of the fingers 304a, 304e and 304f, etc. As will be understood in view of this disclosure, varying the stiffness of the ring 312 in this manner can produce a desired boundary loading on the TS during test, e.g., no net torque and/or each finger applying an equal amount of force to hold the TS in place during testing. It will also be understood that there are a variety of structural optimization methods/techniques known in the art which can be utilized in view of the disclosure for the purpose of producing a desired boundary condition for a hollow tube during testing. For example, a Finite Element Model (FEM) approach may used to determine the appropriate stiffness distribution for a test article and mounting system in view of this disclosure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An apparatus for determining the mechanical properties of a material, comprising:
   a base platform including a programmable drive configured to move relative to a stationary post;
   a test specimen including a hollow cylindrical tube substantially formed from the material and having a first end and a second end; and
   a test fixture, including:
      a first mount coupled to the drive and extending upwards therefrom, the first mount including at an upper end thereof a first member applying pressure about the circumference of the hollow tube first end,
      a second mount coupled to the post and disposed over the drive, the second mount including at an upper end thereof a second member applying pressure about the circumference of the hollow tube second end, and
      a platform connecting the first mount to the drive, and a test bed connecting the second mount to the stationary post and extending over the platform;
   wherein the first mount further includes a standoff connected to the platform at a first end of the standoff, and a clamp assembly connected to a second end of the standoff, wherein the test bed is disposed between the clamp assembly and the platform.

2. The apparatus of claim 1, wherein the test bed includes passageways for allowing the standoff to translate relative to the test bed.

3. The apparatus of claim 1, wherein the clamp assembly includes a clamp applying pressure about the circumference of the hollow tube first end and the clamp is situated along the line of action of the drive.

4. The apparatus of claim 1, wherein the test fixture is configured such that one of a tensile load or transverse load is applied to the tube when the drive moves relative to the post.

5. The apparatus of claim 1, further including a DMA comprising the base, drive and post, wherein the drive is coupled to a device that inputs a deflection to the drive and another device configured to measure the reaction force of the hollow cylindrical tube to the drive deflection.

6. The apparatus of claim 1, wherein the first mount includes means for applying a uniform pressure to the outer circumference of the tube without preloading the tube.

7. An apparatus for determining the mechanical properties of a material, comprising:
   a base platform including a programmable drive configured to move relative to a stationary post;
   a test specimen including a hollow cylindrical tube substantially formed from the material and having a first end and a second end; and
   a test fixture, including:
      a first mount coupled to the drive and extending upwards therefrom, the first mount including at an upper end thereof a first member applying pressure about the circumference of the hollow tube first end, and
      a second mount coupled to the post and disposed over the drive, the second mount including at an upper end thereof a second member applying pressure about the circumference of the hollow tube second end;
   wherein the first mount comprises a clamp capable of restraining an extruded polymer hollow cylindrical tube during a mechanical analysis without imparting a net torque on the tube sufficient to change the mechanical properties of the tube to affect a measurement of a mechanical property of the material, the clamp including
   a ring connecting two arms, and
   a plurality of fingers defining a bearing surface, the plurality of fingers forming an approximately circular bearing surface when the arms are brought adjacent to each other, wherein the stiffness of the ring is varied between one or more fingers to produce the desired boundary condition during testing.

8. The apparatus of claim 7, wherein the clamp further includes a peg surrounded by the fingers.

9. The apparatus of claim 8, wherein the tube is a stent tube.

10. The apparatus of claim 7, wherein the tube is a polymer hollow cylindrical tube having an outer diameter in the range of 0.04-0.2" and an inner diameter in the range of 0.01-0.18" with a length of about 0.5-2".

11. An apparatus for determining the mechanical properties of a material, comprising:
    a base platform including a programmable drive configured to move relative to a stationary post;
    a test specimen including a hollow cylindrical tube substantially formed from the material and having a first end and a second end; and a test fixture, including:
   a first mount coupled to the drive and extending upwards therefrom, the first mount including at an upper end thereof a first member applying pressure about the circumference of the hollow tube first end, and
   a second mount coupled to the post and disposed over the drive, the second mount including at an upper end thereof a second member applying pressure about the circumference of the hollow tube second end;
the first mount further including means for applying a uniform pressure to the outer circumference of the tube without preloading the tube including a ring member having a plurality of radial bearing surfaces and a plurality of T-shaped sections separating the bearing surfaces.

12. An apparatus for testing properties of a material, comprising:
   a DMA;
   a hollow cylindrical tube made from the material and suited for forming a medical prosthesis;
   a fixture mounted within the DMA, the fixture including a clamp holding the tube, the clamp being capable of restraining without imparting a torque preload on the tube or otherwise changing the mechanical properties of the unloaded tube when restrained by the clamp, the clamp including
      two arms,
      a plurality of radial extending fingers having surfaces defining an inner diameter and adapted for gripping the tube outer surface,
      a connector extending between the arms and configured for selectively reducing/enlarging the inner diameter by changing the distance between the arms,
      a flexible coupling extending between the fingers and adapted for producing a load distribution among the fingers that produces a desired boundary condition, and
      a post disposed within the inner diameter and received within the bore of the tube.

13. The apparatus of claim 12, wherein the flexible coupling is a ring having sections of unequal thickness extending between a first and second finger and a third and fourth finger.

14. The apparatus of claim 12, wherein the fingers include tapered ends comprising the surfaces and each of the ends are separated by a gap when the fingers are not gripping the tube.

15. The apparatus of claim 12, the fixture further including a plate, the clamp being fixed to the plate by a connector connecting one of the two arms to the plate, wherein the clamp grips the tube by moving the other of the two arms towards the one arm using a threaded fastener.

* * * * *